US00PP17170P2

(12) United States Plant Patent
Korlipara

(10) Patent No.: US PP17,170 P2
(45) Date of Patent: Oct. 24, 2006

(54) ***VERBASCUM* PLANT NAMED 'HONEY DIJON'**

(50) Latin Name: ***Verbascum* hybrid ((*phoeniceum*×*dumulosum*)×*phoeniceum*))**
Varietal Denomination: Honey Dijon

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 24 days.

(21) Appl. No.: 11/153,519

(22) Filed: Jun. 14, 2005

(51) Int. Cl.
*A01H 5/00* (2006.01)

(52) U.S. Cl. ..... Plt./263

(58) Field of Classification Search ..... Plt./263, Plt./226

See application file for complete search history.

*Primary Examiner*—Kent Bell
(74) *Attorney, Agent, or Firm*—Klarquist Sparkman, LLP

(57) ABSTRACT

A new and distinct *Verbascum* plant characterized by short branched flowering stems of numerous gold colored flowers with purple centers.

1 Drawing Sheet

Botanical classification: *Verbascum* hybrid ((*phoeniceum*×*dumulosum*)×*phoeniceum*)).

Variety denomination: 'Honey Dijon'.

The present invention relates to a new and distinct cultivar of *Verbascum* hybrid, and given the cultivar name 'Honey Dijon'. *Verbascum* is in the family Scrophulariaceae.

This new cultivar originated from a cross between *Verbascum* 'Jackie' (an unpatented plant) as the seed parent and an unnamed selection of *Verbascum phoeniceum* as the pollen parent. *Verbascum* 'Jackie' is an unpatented plant originating from a cross between *Verbascum phoeniceum* and *Verbascum dumulosum*.

This new *Verbascum* hybrid is unique in its gold flower color combined with its *Verbascum* 'Jackie'-like compact habit and short, multiple flowering stems.

This plant is characterized by the following:

1. Large fold flowers with dark eyes.
2. Numerous upright flowering stems.
3. Compact habit.
4. Short flowering stems.
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a close up of *Verbascum* 'Honey Dijon' growing in the ground in the trial fields in full sun in July in Canby, Oreg.

DETAILED PLANT DESCRIPTION

The following is a detailed description of the new *Verbascum* selection based on observations of one-year-old specimens in the ground in full sun under typical outdoor conditions in the field in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Type.*—Herbaceous perennial.
*Form.*—Clumping basal rosette.
*Hardiness.*—U.S.D.A. Hardiness Zones 5–9.
*Size.*—11 cm tall and 40 cm wide, not including inflorescence.
*Vigor.*—Excellent.
*Roots.*—With one main tap root, and many fibrous lateral branches, White 155A.
*Stem.*—Much congested, 1 cm deep and wide with no space between internodes.

Leaf:

*Type.*—Simple, evergreen.
*Arrangement.*—Basal, with 35 to 40 leaves.
*Shape.*—Lanceolate.
*Blade size.*—Grows to 16 cm long and 6.3 cm wide.
*Venation.*—Pinnate.
*Margins.*—Irregularly crenate overall and toothed near base.
*Apex.*—Acute.
*Base.*—Obtuse to oblique.
*Surface texture.*—Leathery, soft, with stellate and velutinous hairs on both sides.
*Petiole description.*—6 to 11 cm long and 8 mm wide, eye-shaped in cross section, with stellate and velutinous hairs, Yellow Green 145A to 145C with a pinker color up the middle, Greyed Purple 186C.
*Leaf color.*—Topside — Deep green. Closest to Green 147A with a prominent main vein, Yellow Green 145A to C with a pinker color in the middle, Greyed Purple 186C. Bottom side — Yellow Green 147B.

Inflorescence:

*Type.*—Panicle with 4 side branches.

*Number.*—Up to 8 panicles per plant in the first flush.

*Size.*—Each panicle is up to 9 cm wide and 48 cm high.

*Cauline leaves.*—10 to 12 in number, 1.4 to 12 cm long (including petiole on lower leaves, upper leaves sessile) and 1.5 to 4 cm wide, decreasing in size as the go up the stem.

*Flower number.*—About 300 flowers per panicle.

*Peduncle description.*—60 cm tall, 7 mm wide near the base, stellate tomentum below flowers and glandular where flowers are present, Yellow Green 146A.

*Pedicel description.*—1.5 cm long, with glandular hairs, Yellow Green 146C.

*Bloom time.*—July through August in Canby, Oreg.

Flower bud:

*Size.*—1.1 cm. wide and 0.7 cm. deep.

*Description.*—Pentagonal cushion.

*Surface.*—Glandular pubescent.

*Color.*—Greyed Purple 183A when small to Greyed Orange 174A.

Flower:

*Type.*—Perfect, complete, irregular.

*Shape.*—Rotate, irregular, short tubular.

*Size.*—3 cm wide and 1.1 cm deep including stamens.

*Color.*—Gold, Yellow Orange 22A with a purple eye, Greyed Purple 187B, with some Greyed Orange 174A on backs.

*Corolla.*—Petal description — 5 lobes, broadly obovate, margin entire, tip obtuse, base cuneate. Size — 3 cm wide and 0.4 cm deep. Surface — Backs glandular.

*Calyx.*—Sepal description — Stellate, with 5 lobes, each lobe lanceolate with entire margins and an acuminate tip. Size — Grows to 1.2 cm. wide and 0.2 deep. Surface — Glandular pubescent on both surfaces. Color — Yellow Green 146A on both upper and lower surfaces.

*Stamens.*—Number — 5. Filaments — 0.7 cm long, Yellow Orange 14A at base Greyed Purple 187B for the rest, heavily bearded Purple 77A on lower two stamens and Purple 77A topped with White 155A on upper three stamens. Anthers — Kidney shaped. Greyed Purple 187A on top and Greyed Orange 163C to D on the bottom, 2 mm long. Pollen — Orange 24A, abundant in quantity.

*Pistil.*—Number — 1. Size — 1.1 cm long. Style color — Greyed Purple 185A. Stigma — blunt, Yellow Green 146C. Ovary — Yellow Green 146C.

*Fragrance.*—None.

Fertility: Female sterile, no fruit or seed produced.

Disease: All *Verbascum* are subject to root rots in poorly drained soil. Powdery mildew is also a problem. *Verbascum* are susceptible to caterpillars.

COMPARISONS

This new cultivar is very similar in growth habit and flowering habit to *Verbascum* 'Jackie' (an unpatented plant). The greatest difference is the flower color.

*Verbascum* 'Jackie' is described as having copper colored buds that open to pale peach colored flowers and lavender stamens. The new cultivar *Verbascum* 'Honey Dijon' has maroon to brown buds and gold colored flowers. The foliage of the new cultivar is larger.

Compared to the pollen parent, *Verbascum phoeniceum,* the new cultivar has shorter flowering stems, larger leaves and flowers, longer bloom time, longer life span, and gold rather than pink colored flowers.

I claim:

1. A new and distinct variety of *Verbascum* plant as herein illustrated and described.

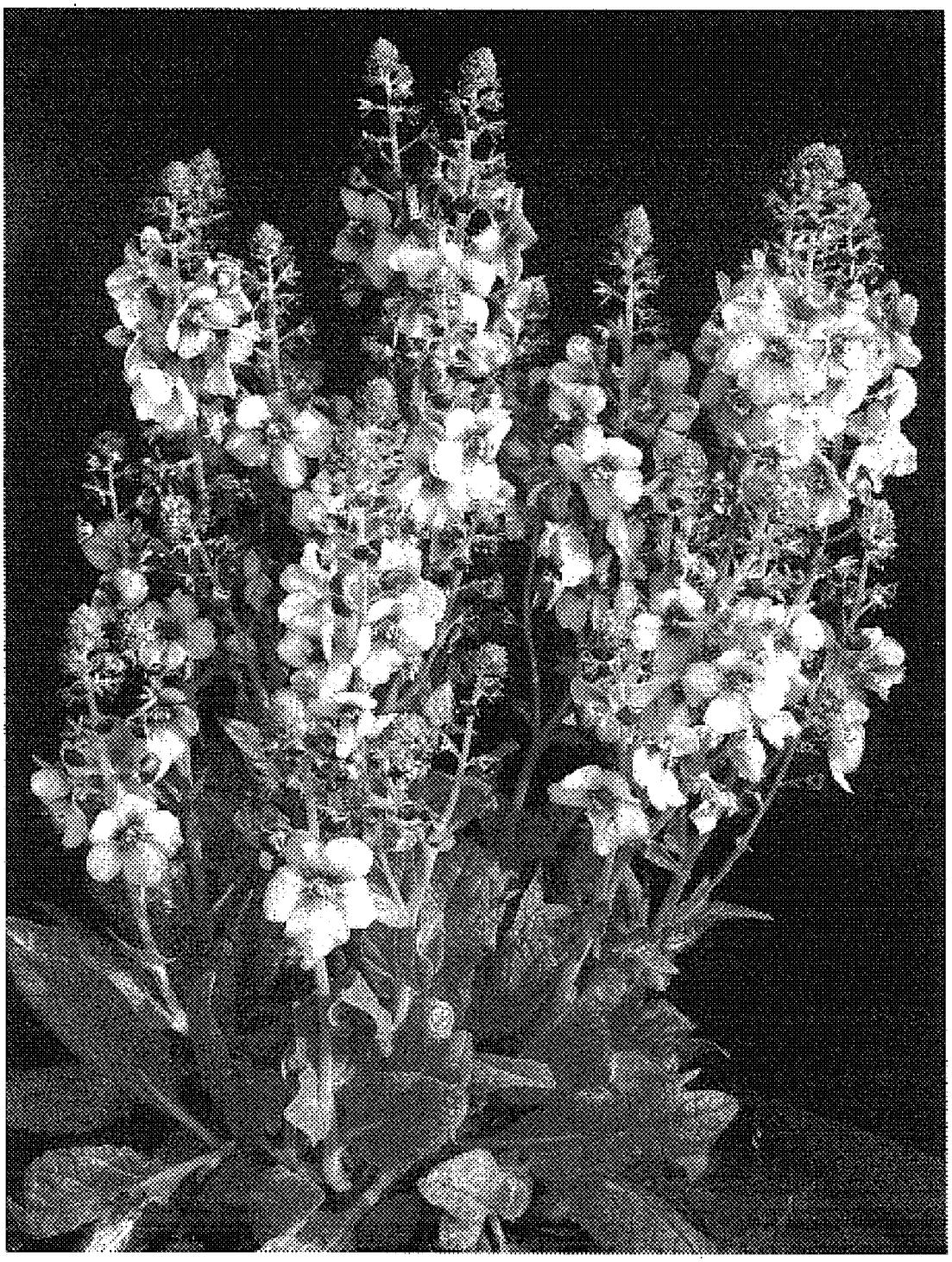

* * * * *